(12) United States Patent
Bahr et al.

(10) Patent No.: US 6,767,635 B1
(45) Date of Patent: Jul. 27, 2004

(54) MAGNETIC NANOPARTICLES HAVING BIOCHEMICAL ACTIVITY, METHOD FOR THE PRODUCTION THEREOF AND THEIR USE

(75) Inventors: Michael Bahr, Weimar (DE); Dimitri Berkov, Jena (DE); Norbert Buske, Berlin (DE); Joachim Clement, Jena (DE); Peter Görnert, Jena (DE); Klaus Höffken, Weimar (DE); Kay-Oliver Kliche, Zöllnitz (DE); Thomas Kober, Berlin (DE); Matthias Schnabelrauch, Jena (DE); Sebastian Vogt, Jena (DE); Kerstin Wagner, Jena (DE); Christian Gansau, Nieder-Neuendorf (DE)

(73) Assignee: Biomedical Apherese Systeme GmbH, Jena (DE)

( * ) Notice: Subject to any disclaimer, the term of this patent is extended or adjusted under 35 U.S.C. 154(b) by 0 days.

(21) Appl. No.: 10/088,437

(22) PCT Filed: Sep. 14, 2000

(86) PCT No.: PCT/EP00/09004

§ 371 (c)(1),
(2), (4) Date: May 24, 2002

(87) PCT Pub. No.: WO01/19405

PCT Pub. Date: Mar. 22, 2001

(30) Foreign Application Priority Data

Sep. 14, 1999 (DE) ......................................... 199 44 971

(51) Int. Cl.[7] .................................................. B32B 5/16
(52) U.S. Cl. .................. 428/402; 428/403; 428/402.24; 428/407; 428/694 BA; 436/524; 436/525; 436/526; 436/527; 435/6; 435/7.5; 435/7.21
(58) Field of Search ............................ 428/402, 402.24, 428/403, 407, 694 BA; 436/524, 525, 526, 527; 435/6, 7.5, 7.21

(56) References Cited

U.S. PATENT DOCUMENTS

| | | | | |
|---|---|---|---|---|
| 5,248,589 A | * | 9/1993 | Bose et al. | 435/2 |
| 5,665,582 A | * | 9/1997 | Kausch et al. | 435/181 |
| 6,521,773 B1 | * | 2/2003 | Hainfeld | 556/147 |
| 6,548,264 B1 | * | 4/2003 | Tan et al. | 435/7.21 |

* cited by examiner

*Primary Examiner*—Leszek Kiliman
(74) *Attorney, Agent, or Firm*—Norris McLaughlin & Marcus

(57) ABSTRACT

The invention relates to magnetic nanoparticles, their production, and their use.

The object of the invention is to provide nanoparticles capable of specifically forming bonds to intracellular biomacromolecules even in the intracellular region of cells, so that separation is possible by exposure to an exterior magnetic field.

This is accomplished by means of magnetic nanoparticles having biochemical activity, consisting of a magnetic core particle and an envelope layer fixed to the core particle, and including a compound of general formula M-S-L-Z (I), the linkage sites between S and L and L and Z having covalently bound functional groups, wherein M represents said magnetic core particle;
S represents a biocompatible substrate fixed to M;
L represents a linker group; and
Z represents a group comprised of nucleic acids, peptides or proteins or derivatives thereof, which group has at least one structure capable of specifically binding to a binding domain of an intracellular biomacromolecule.

22 Claims, No Drawings

MAGNETIC NANOPARTICLES HAVING BIOCHEMICAL ACTIVITY, METHOD FOR THE PRODUCTION THEREOF AND THEIR USE

BACKGROUND OF THE INVENTION

The invention relates to magnetic nanoparticles, their production, and their use.

The most frequent causes of death include cancers. In particular, more and more people die from lung, breast and prostate cancers. Presently, the primary objectives of medicine therefore include the control of cancers.

In addition to operative removal of affected organs, conventional methods of treatment for controlling metastasizing tumors include chemotherapy with its well-known pattern of side effects, because these medications also do damage to healthy cells as a result of their non-specific effects, namely, in susceptible regions throughout the body.

Inter alia, new approaches of therapy utilize immune reactions in such a way that, on the one hand, endogenous resistance is activated by messenger substances or cytokines and, on the other hand, protein molecules and/or monoclonal antibodies destroy the tumor cells.

New developments in the field of tumor cell separation already use particles including a magnetic core, which particles are modified with biologically active envelope substances. So-called "drug targeting" using substances such as doxorubicin or other cytostatic agents coupled to magnetic microspheres is in development. "Microbeads" and "dynabeads", also well-known, are already being used in diagnostic methods wherein magnetic micro-spheres are adsorbed on the cell membrane of malignant cells by biological interaction and subsequently subjected to magnetic separation. In general, the surface structure of cell membranes is non-specific and therefore, however, the separation rates are less than 80%. As a consequence, there is a risk in that many cancer cells will not undergo separation, maintaining their ability of forming metastases.

Separation for diagnostic purposes is invariably performed on the extracorporeal route, i.e., the fluid including the cells to be separated is treated in a suitable vessel outside the human body. Following separation, the purified liquid can be re-supplied into the human body.

Due to incomplete separation of malignant cells, it must be expected that this procedure has to be repeated after some time. This procedure does severe stress to persons who are sick anyway, so that repeated treatment is possible to only a limited extent.

DE 41 16 093 A1 describes a method of obtaining magnetic carriers by controlled modification of the surface of magnetic particles. According to this method, magnetic particles are described which can also form magnetic fluids, and which are characterized in that they carry heteropolyanions and saturated or unsaturated surface-active agents. Such surface modification is intended to permit binding of biologically active molecules such as antibodies, among others, to the surface of the particles. The biologically active molecules are bound to polythiols via thio bridges. Inter alia, dicar-boxylic acids and hydroxycarboxylic acids, as well as dimer-captosuccinic acid are used as linker substances. Owing to an iron-chelating group, these compounds are capable of binding to the magnetic particle.

Having insufficient biocompatibility, these magnetic particles including biologically active molecules on their surface were found unsuitable for the purpose of permeating into intracellular compartments to couple with biomacromolecules therein.

DE 196 24 426 A1 describes magnetic fluids used to transport diagnostically or therapeutically active substances. The magnetic core particles are enveloped with polymers having reactive groups capable of covalent binding or ion exchange. On this envelope, which indeed is biocompatible and may consist of dextran, among other things, new or additional functional groups can be attached or activated, e.g. succinic anhydride or chloroacetic acid, to which diagnostically or therapeutically active substances then can be fixed either via a heteropolar or a covalent bond. The pharmaceutical agent bound to the magnet particle in the way as described should be administrable on the intravenous route and is to be fixed by means of a high-gradient magnetic field within the region of a target area such as a tumor or an inflammatory tissue region to develop its diagnostic and therapeutic effects therein. To enable such transport in a magnetic field, high intravascular availability of the magnet particles is required, the particle size of which being specified as 200-500 nm. In this case as well, the particles are incapable of permeating into intracellular compartments due to the mere size of the particles. Moreover, specific binding to intracellular biomacromolecules is not feasible with these particles.

SUMMARY OF THE INVENTION

The object of the invention is to provide nanoparticles capable of specifically forming bonds to intracellular biomacromolecules even in the intracellular region of cells, so that separation is possible by exposure to an exterior magnetic field.

According to the invention, said object is accomplished with the characterizing sections of claims 1, 9, 13, 17, 18, 19, 21, and 23 to 25.

DETAILED DESCRIPTION OF THE PREFERRED EMBODIMENTS

Advantageously, the magnetic nanoparticles of the invention are capable of permeating through cell membranes and into intracellular compartments to interact with intracellular biomacromolecules therein.

The magnetic nanoparticles consist of a ferri- or ferromagnetic material and have biologically active and/or therapeutically effective envelope layers. On the one hand, they are able to permeate the cell membrane of cells and, on the other hand, to attach with high specificity to targets present in the intracellular region of malignant cells.

As a rule, the size of the nanoparticles according to the invention is from 2 to 100 nm. The nanoparticles have out-standing properties with respect to their capability of permeating cell membranes and their improved physical compatibility. Although having a relatively low magnetic moment as a result of their small volume, intracellular particle agglomeration caused by binding to intracellular target biomacromolecules results in an augmented concentration with increased magnetic moment of the malignant cells to be removed, thereby promoting magnetic separation.

Typical core materials of the nanoparticles according to the invention are ferrites of general composition $MeO_xFe_2O_3$ wherein Me is a bivalent metal such as Co, Mn or Fe. Other suitable materials are $\gamma\text{-}Fe_2O_3$, the pure metals Co, Fe, Ni, and metal compounds such as carbides and nitrides.

The magnetic moment of cobalt and iron is up to four times higher than that of ferrites and therefore, given same particle size and same magnet field, these materials are removed more effectively. However, it must be considered that the biological compatibility of these materials is lower. This could be an advantage if additional damage is done to e.g. malignant cells in this way. On the other hand, the time of exposure to and concentration of these substances in healthy cells must be limited.

The interplay of biochemical, medical and physical properties requires producing tailored magnetic core materials and envelope layers.

According to the invention, the magnetic nanoparticles according to claim 1 enable permeation of the cell membranes and interaction of the magnetic nanoparticles with intracellular target biomacromolecules. To this end, homogeneous dispersion of the magnetic nanoparticles in body fluids is necessary, because aggregated nanoparticles are incapable of permeating the cell membrane. Inter alia, this requires an envelope layer of sufficient thickness which must be at least in the range of the core radius, and good biocompatibility of the envelope layer components. Charge carriers in the envelope material, i.e., an increased zeta potential, may have an additional beneficial effect on the dispersibility in a body fluid.

A particularly beneficial administration form of the magnetic nanoparticles is a dispersion in accordance with claim 9.

Homogeneous distribution of the magnetic nanoparticles according to the invention can be promoted by adjusting a low concentration in the nanoparticle dispersions. However, higher concentrations are generated in the interior of the cell when the nanoparticles are concentrated by specific adsorption on target biomacromolecules in the intracellular region of cells. Such particle agglomeration is advantageous in the interior of a cell. As a result of the higher concentration of magnetic nanoparticles, the magnetic moment in the cells to be separated is increased.

The magnetic core particles are formed either in aqueous or in organic phase via nucleation/crystal growth processes. Preparation in the aqueous phase using chemical precipitation methods involves several advantages. Non-modified magnetic particles are formed in a first step, and these particles may acquire both positive and negative signs of charge by adjusting the pH. Only then, the envelope molecules are adsorbed in a second step. The adsorption effectiveness depends on the sign of charge on the surface of the magnetic core particles. As a rule, envelope molecules having negatively charged molecule portions preferably adsorb to core surfaces having a positive sign of charge. In most of these cases, an ionic chemical reaction is effected, including e.g. carboxyl compounds and amino compounds. Such a reaction is advantageous in that, on the one hand, the adsorbed envelope molecules completely cover the core surface and, on the other hand, are anchored firmly thereon.

Frequently, coordinative binding of the biocompatible substrate S is insufficient for firm anchoring, as is known with polysaccharides.

The preparation of ferromagnetic metal core particles is predominantly effected using thermolysis of the corresponding metal carbonyls in organic phase. To this end, surfactants or polymers soluble in the organic phase are added for stabilization. In a first reaction step, core particles are formed which are homogeneously dispersed in the organic phase. In a second reaction step, the core particles are transferred into an aqueous carrier fluid. If the envelope layer includes modified amino acids, said transfer of core particles is performed after extensive removal of the organic solvent by adding alkaline aqueous carrier fluid. The envelope layer is converted to a water-soluble salt of the amino acid which causes dispersion of the magnetic core particles. Subsequently, the magnetic nanoparticles can be produced via further reactions.

According to the invention, the magnetic nanoparticles include a compound of general formula M-S-L-Z (I), the linkage sites between S and L and L and Z having covalently bound functional groups, wherein M represents the magnetic core particle;

S represents a biocompatible substrate fixed to M;

L represents a linker group, and

Z represents a group comprised of nucleic acids, peptides or proteins or derivatives thereof, which group has at least one structure capable of specifically binding to a binding domain of an intracellular biomacromolecule.

The magnetic core particles consist of magnetite, maghemite, ferrites of general formula $MeO_xFe_2O_3$ wherein Me is a bivalent metal such as cobalt, manganese, iron, or of cobalt, iron, nickel, iron carbide, or iron nitride. In a further development of the invention, the size of the core particles is from 2 to 100 nm.

In one embodiment of the invention, the substrate S is formed by compounds such as poly- or oligosaccharides or derivatives thereof, such as dextran, carboxymethyldextran, starch, dial-dehyde starch, chitin, alginate, cellulose, carboxymethylcellulose, proteins or derivatives thereof, such as albumins, peptides, synthetic polymers, such as polyethyleneglycols, polyvinylpyrrolidone, polyethyleneimine, polymethacrylates, bifunctional carboxylic acids and derivatives thereof, such as mercaptosuccinic acid or hydroxycarboxylic acids.

In another embodiment of the invention, the linker group L is formed by reaction of a compound such as poly- and dicarboxylic acids, polyhydroxycarboxylic acids, diamines, amino acids, peptides, proteins, lipids, lipoproteins, glycoproteins, lectins, oligosaccharides, polysaccharides, oligonucleotides and alkylated derivatives thereof, and nucleic acids (DNA, RNA, PNA) and alkylated derivatives thereof, present either in single-stranded or double-stranded form, which compound includes at least two identical or different functional groups.

In another exemplary variant of the invention, functional groups are provided as examples which, according to the invention, can be used as linkage groups for the substrate S, for the linker group L, and for group Z. It is crucial that compound (I) is characterized by covalent bonds.

The biochemically active compound of general formula S-L-Z (II) is excellently suited for producing the magnetic nanoparticles according to the invention.

The production of the magnetic nanoparticles is performed in steps. The magnetic core particles are produced in a per se known manner and, in a preferred variant, reacted directly with the biochemically active compound (II).

In another embodiment of the invention, the magnetic core particles are produced according to the following method:

a. producing the magnetic core particles in a per se known manner;

b. reacting the magnetic core particles with the biocompatible substrate S; and c. reacting the compound M-S having formed with a compound L-Z;

wherein in order to produce L-Z, a compound such as poly- and dicarboxylic acids, polyhydroxycarboxylic acids, diamines, amino acids, peptides, proteins, lipids, lipoproteins, glycoproteins, lectins, oligosaccharides, polysaccharides, oligonucleotides and alkylated derivatives thereof, and nucleic acids (DNA, RNA, PNA) and alkylated derivatives thereof, present either in single-stranded or double-stranded form, which compound includes at least two identical or different functional groups, is reacted with nucleic acids, peptides and/or proteins or derivatives thereof having at least one functional group and including at least one structure capable of specifically binding to a binding domain of an intracellular biomacromolecule.

The procedure for producing the biochemically active compound (II) is such that compound L-Z is produced first, and L-Z subsequently is reacted with the substrate S.

The nanoparticles according to the invention can be used in the separation of cells, in the separation of malignant cells, and in the separation of intracellular biomacromolecules. In particular, the fusion regions of chromosomes as molecular markers are intended to serve as points of attack for interaction with intracellular biomacromolecules. For example, these can be molecular markers typical for a particular disease. Furthermore, these fusion regions may lead to fusion genes producing fusion messenger ribonucleic acids (fusion mRNA) and fused proteins. The chronic myeloid leukemia (CML) may be mentioned as an example. In CML, a chromosomal rearrangement t(9;22) (q34;q11) occurs, the so-called Philadelphia chromosome which leads to the BCR/ABL gene product. That is, in cells with such a chromosomal aberration, a gene is present which occurs in no other body cell. This gene is transcribed to messenger ribonucleic acid (mRNA), resulting in the synthesis of the BCR/ABL protein. BCR/ABL mRNA and BCR/ABL protein exclusively occur in tumor cells. BCR/ABL mRNA is possible as binding domain for the magnetic nanoparticles. The Z group of the magnetic nanoparticles according to the invention is to interact with the complementary sequence on the mRNA via nucleic acid/nucleic acid interaction, said sequence being required to include the BCR/ABL fusion site. The individually specific sequence around the fusion site is determined previously using laboratory methods. The interaction is to take place in the cytoplasm of tumor cells. Once the magnetic nanoparticles have attached via the Z group to the complementary sequence on the BCR/ABL mRNA, the tumor cell is labelled.

Other exemplary cancers are mentioned below:

| Hematological disease | Chromosomal rearrangement (Fusion gene product) |
|---|---|
| Acute lymphatic leukemia (ALL) | t(9;22) (q34;q11) (BCR/ABL) |
| | t(1;19) (q23;p13) (E2A/PBX) |
| | t(8;14) (q24;q32) |
| | t(2;8) (p11;q24) |
| | t(8;22) (q24;q11) (MYC, IGH, IGK, IGL) |
| | t(4;11) (q21;q23) (MLL/AF2) |
| | t(1;14) (p32;q11) del(1p32) (TAL1, TCRA) |
| Acute myeloid leukemia (AML) | t(8;21) (q22;q22) (AML/ETO) |
| | t(15;17) (q21;q11) (PML/RARA) |
| | inv16(p13;q22) t(16;16) (p13;q22) (MYH11/CBFb) |
| | t(6;9) (p23;q34) (DEK/CAN) |

-continued

| Hematological disease | Chromosomal rearrangement (Fusion gene product) |
|---|---|
| Non-Hodgkin lymphoma | (14;18) (q32;q21) (BCL2/IGH) |
| | t(8;14) (q24;q32) |
| | t(2;8) (p11;q24) |
| | t(8;22) (q24;q11) (MYC, IGH, IGK, IGL) |
| | t(11;14) (q13;q32) (BCL1/IGH) |
| | t(3;14) (q27;q32) (BCL6/IGH) |
| Ewing's sarcoma | t(11;22) (q24;q12) (FLI1/EWS) |

For these diseases, which merely represent a choice of possible diseases to be treated by therapy, the above procedure is used in analogy. For each disease, there is one typical base sequence which is unequivocally described by the following chromosomal sites. In these diseases as well, the Z group of the magnetic nanoparticles is to interact accordingly with the complementary sequence (binding domain) on the mRNA via nucleic acid/nucleic acid interaction. The number of all the precise base sequences for any possible disease is infinite; and for CML alone, more than 10 breakage regions have been described to date, and new ones are constantly being described.

The invention has various advantages. Firstly, the magnetic nanoparticles of the invention were found to have high biocompatibility in corresponding cell culture investigations. This enables safe application, and also, a purely extracorporeal application of the particles is possible within the scope of uses according to the invention. In contrast to existing separation methods using flow cytometry (FACS) and magnetic separation (MACS), the magnetic nanoparticles of the invention offer crucial advantages. By their use, it is possible to reach the interior of cells, the so-called cytoplasm, and effect specific binding of biomacromolecules with corresponding structures such as binding domains of nucleic acids. Likewise, proteins being formed upon appropriate translation are contemplated as target biomacromolecules for specific binding to the Z group of general formula (I). According to current knowledge, all of these malignant diseases are based on an aberrant genome in the cell. In a number of diseases, this molecular basis has already been defined. The fusion of existing genes to form so-called fusion genes results in an individually specific change in the base sequence which is specific both with respect to the basic disease and the respective patient. According to the invention and within the scope of this procedure, the altered genomic structure (binding domain) as specific binding counterpart of the Z group in (I) is defined at first, using molecular diagnostics. Thereafter, the Z group as specific binding counterpart of the binding domain is synthesized and subsequently put to clinical use. Furthermore, it should be noted that healthy cells as well have well-defined base sequences which are of interest as binding domains. Embryonic cells may serve as an example, which cells are present in any healthy organism and, being a prototype of cell type-specific gene expression, have a base sequence different from that of adult cells. These cells—as well as malignant cells—can be used as target objects in magnetic separation of intracellular biomacromolecules by specific binding of the Z group to intracellular nucleic acids. Thus, it is clear that separation of malignant cells is only one example among many others. In addition to removal from blood, the use on any other body fluid such as cerebrospinal fluid, lymph, urine, saliva, sperm, as well as dissociated tissues is possible.

The inventive use of magnetic nanoparticles will be illustrated in more detail once again, using the example of chronic myeloid leukemia.

For quite a long time, chronic myeloid leukemia is known to be based on a specific translocation between chromosomes 9 and 22, referred to as Philadelphia chromosome as a general term. However, molecular analyses in recent years have shown that even in one particular disease, a multiplicity of possible breakage sites, i.e., different fusion genes, are present which must be defined individually in each patient. Consequently, there is no way of offering a universal strategy for any patient suffering from chronic myeloid leukemia, but rather, the precise location of the breakage sites (binding domain) has to be defined first in the way as described above. Advantageously following appropriate characterization, the breakage sites are to be addressed specifically with the magnetic nanoparticles according to the invention. Now, the cells of the malignant clone can be labelled, followed by separation in the desired manner. In principle, this procedure is possible with all the other diseases. Solid tumors such as breast carcinoma or colon carcinoma are also increasingly understood in their molecular fundamentals. Hereditary forms of breast and intestinal cancers can be discerned from sporadic forms which still represent by far the largest number of cases. Again, using expression of particular gene patterns, malignant cells can be labelled and isolated in the desired form. In principle, extraction both from fluids and tissues is possible. At this point, it should be noted once again that no other magnetic nanoparticle allows performing such a specific procedure which represents a completely new way of utilizing binding of magnetic particles to biomacromolecules.

The invention will be illustrated in more detail with reference to the following examples.

EXAMPLES

Example 1

0.5mol $FeCl_2 \cdot 4H_2O$ and 1 mol $FeCl_3 \cdot 6H_2O$ are completely dissolved in 100 ml of water and added with concentrated ammonium hydroxide with stirring until a pH value of 9 is reached. The black particles in the dispersion are separated by magnetic means, and the supernatant is decanted. Thereafter, the dispersion is brought to pH 1–4 using half-concentrated HCl, thereby exchanging the particle charges. This process is repeated until the particles begin to redisperse. Subsequently, this is centrifuged (5,000 to 10,000 g), and the supernatant low in particles is decanted. The residue is taken up in HCl (3–10 N), and the complete process is repeated until an electric conductivity of 20–500 $\mu$S/cm at a pH value of 4–5 is reached, or, the residue is dialyzed against HCl (3–10 N) until the same values are reached.

The saturation polarization of the stable magnetite/maghemite sol having formed is 6 mT at maximum.

Example 2

0.5 mol $FeCl_2 \cdot 4H_2O$ and 1 mol $FeCl_3 \cdot 6H_2O$ are completely dissolved in 100 ml of water and added with concentrated ammonium hydroxide with stirring until a pH value of 9 is reached. The black particles in the dispersion are separated by magnetic means, and the supernatant is decanted. Subsequently, this is added with some milliliters of hydrogen peroxide (30%), thereby oxidizing the particles to form maghemite. Thereafter, the particles are treated by adding half-concentrated HCl as described in Example 1.

The saturation polarization of the stable maghemite sol having formed is 6 mT at maximum.

Example 3

100 ml of the magnetite and/or maghemite sol described in Examples 1 and 2 is added with 6 g of CM-dextran (DS 0.4–2) dissolved in 20 ml of water, and the mixture is heated with stirring at 40–80° C., preferably 50–60° C., for 30 minutes. The stable sol being formed, consisting of magnetite/maghemite particles coated with CM-dextran, is subsequently purified using dialysis against water.

Example 4

To a solution of 0.6 g of CM-dextran (DS 0.4–2) in 25 ml of water, 13.1 ml of a 1 M Fe(III) chloride solution including 2.04 g of $FeCl_2 \cdot 4H_2O$ dissolved therein is slowly added dropwise at 70° C. with stirring. Thereafter, the reaction mixture is brought to pH 9–10 by adding dilute NaOH (2N), and this is subsequently neutralized with dilute HCl (2N) and stirred for 2 hours at 70° C., the pH value of the solution being maintained at about 6.5–7.5 by further addition of dilute NaOH or HCl. The reaction mixture is cooled, followed by removal of insolubles by centrifugation, and the magnetic fluid obtained is purified using dialysis against water.

The saturation polarization of the nanoparticles coated with CM-dextran is 6 mT at maximum.

Example 5

100 ml of the magnetite and/or maghemite sol described in Examples 1 and 2 is added with 2 g of dimercaptosuccinic acid dissolved in 20 ml of water, and the mixture is heated with stirring at 70° C. for 30 minutes. The stable sol being formed, consisting of magnetite/maghemite particles coated with dimercaptosuccinic acid, is subsequently purified using dialysis against water. The saturation polarization is 1–8 mT, preferably 3–6 mT.

Example 6

100 ml of the magnetite and/or maghemite sol described in Examples 1 and 2 is added with 6 g of bovine albumin dissolved in 100 ml of water, and the mixture is heated with stirring at 70° C. for 30 minutes. The stable sol being formed, consisting of albumin-coated magnetite/maghemite particles, is subsequently purified using dialysis against water.

Example 7

100 ml of the dispersion produced according to Example 1 or 2 is mixed up in an alkaline solution containing 7 g of N-oleoylsarcosine (Korantin SH from BASF) and stirred for 30 minutes at 50–80° C., preferably at 65° C. The particles agglomerate upon mixing, but re-stabilize when maintaining the pH value in the alkaline range, preferably between 8 and 9. The particles precipitate in the acidic range, but undergo redispersion in the alkaline range.

Example 8

To 1 mg of succinic acid dissolved in 10 ml of water, an equimolar amount of a water-soluble carbodiimide (N-ethyl-N'-(3-dimethylaminopropyl)carbodiimide hydrochloride) is added with stirring, and this is stirred for 30 minutes at 5–10° C. Subsequently, 10 $\mu$g of an amino-functionalized oligonucleotide (5'-$H_2N$-ACTGGCCGCTGAAGGG CTTCTGCGTCTCCA-OH-3') dissolved in 50 $\mu$l of phosphate buffer (pH 7.0) is added, and the mixture is maintained at 5–10° C. for 24 hours. To remove byproducts and non-reacted starting materials, this is dialyzed against water, and the reaction product is lyophilized.

Example 9

To 10 μg of the oligonucleotide functionalized according to Example 8 and dissolved in 100 μl of phosphate buffer (pH 7.0), 20 μg of a water-soluble carbodiimide (N-ethyl-N'-(3-dimethylaminopropyl)carbodiimide hydrochloride) is added with stirring, and this is maintained at 5–10° C. for 30 minutes. Subsequently, this solution is added to 200 mg of albumin dissolved in 20 ml of phosphate buffer, and the mixture is maintained at 5–10° C. for 24 hours. To remove byproducts and non-reacted starting materials, this is dialyzed against water, and the reaction product obtained is lyophilized.

Example 10

1 ml of the magnetite and/or maghemite sol described in Examples 1 and 2 is diluted with water at a ratio of 1:10 and adjusted to pH 7 by adding dilute NaOH. Subsequently, 60 mg of albumin functionalized according to Example 9 and dissolved in 10 ml of phosphate buffer (pH 7.0) is added, and this is heated for about 30 minutes at 40° C. with stirring. The magnetic fluid thus obtained is subsequently centrifuged, and the solution is purified using dialysis against water.

Example 11

To 10 μg of the oligonucleotide functionalized according to Example 8 and dissolved in 100 μl of phosphate buffer (pH 7.0), 20 μg of a water-soluble carbodiimide (N-ethyl-N'-(3-dimethylaminopropyl)carbodiimide hydrochloride) is added with stirring, and this is maintained at 5–10° C. for 30 minutes. Subsequently, this solution is added to 10 ml of the magnetic fluid prepared according to Example 6 and diluted with water at a ratio of 1:10, maintained at 5–10° C. for 24 hours and then purified using dialysis against water.

Example 12

1 ml of the magnetic fluid prepared according to Example 3 or 4 is diluted with water at a ratio of 1:10, added with 20 mg of a water-soluble carbodiimide (N-ethyl-N'-(3-dimethylaminopropyl)carbodiimide hydrochloride), and this is stirred at 5–10° C. for about 30 minutes. Thereafter, 10 mg of a peptide (H-Ala-Ala-Ala-Ala-OH) is added, and the mixture is maintained at 5–10° C. for 24 hours. To remove byproducts and non-reacted starting materials, this is dialyzed against water.

Example 13

To 10 ml of the solution described in Example 12, 20 mg of a water-soluble carbodiimide (N-ethyl-N'-(3-dimethylaminopropyl)carbodiimide hydrochloride) is added, and this is stirred at 5–100C for 30 minutes and added with 10 μg of an amino-functionalized oligonucleotide (see Example 7) dissolved in 50 μl of phosphate buffer (pH 7.0). The mixture is maintained at 5–10° C. for 24 hours and subsequently dialyzed against water.

What is claimed is:

1. Magnetic nanoparticles having biochemical activity, consisting of a magnetic core particle and an envelope layer fixed to the core particle,
wherein
the magnetic nanoparticles comprise a compound of general formula

M-S-L-Z                                (I), the linkage sites between S and L and, L and Z further comprise covalently bound functional groups,
wherein
M represents said magnetic core particle;
S represents a biocompatible substrate fixed to M;
L represents a linker group, and
Z represents a group comprised of nucleic acids, peptides or proteins or derivatives thereof, at least one of which binds to an intracellular biomacromolecule.

2. The magnetic nanoparticles according to claim 1,
wherein
the core particles consist of magnetite, maghemite, ferrites of general formula $MeO_xFe_2O_3$ wherein Me is a bivalent metal selected from the group consisting of cobalt, manganese, iron, of cobalt, iron, nickel, iron carbide, and iron nitride.

3. The magnetic nanoparticles according to claim 1 wherein the size of the core particles is from 2 to 100 nm.

4. The magnetic nanoparticles claim 1,
wherein
the biocompatible substrate S is a compound selected from the group consisting of poly- or oligosaccharides or derivatives thereof, such as dextran, carboxymethyidextran, starch, dialdehyde starch, chitin, alginate, cellulose, carboxymethylcellulose, proteins or derivatives thereof, albumins, peptides, synthetic polymers, polyethyleneglycols, polyvinylpyrrolidone, polyethyleneimine, polymethacrylates, bifunctional carboxylic acids and derivatives thereof, mercaptosuccinic acid or hydroxycarboxylic acids.

5. The magnetic nanoparticles according to claim 1,
wherein
the linker group L is formed by reaction of a compound selected from the group consisting of poly- and dicarboxylic acids, polyhydroxycarboxylic acids, diamines, amino acids, peptides, proteins, lipids, lipoproteins, glycoproteins, lectins, oligosaccharides, polysaccharides, oligonucleotides and alkylated derivatives thereof, and nucleic acids (DNA, RNA, PNA) and alkylated derivatives thereof, present either in single-stranded or double-stranded form, which compound includes at least two identical or different functional groups.

6. The magnetic nanoparticles according to claim 1,
wherein
the functional groups are selected from the group consisting of —CHO, —COOH, —NH$_2$, —SH, —NCS, —NCO, —OH, —COOR,
wherein
R represents an alkyl, acyl or aryl residue and

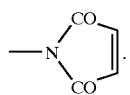

7. The magnetic nanoparticles according to claim 1,
wherein
S and M are covalently linked to each other.

8. The magnetic nanoparticles according to claim 1,
wherein
an electrostatic bond is formed between M and S.

9. A dispersion, comprised of magnetic nanoparticles according to claim 1 and a carrier fluid.

10. The dispersion according to claim 9,
wherein
the carrier fluid includes polar and/or non-polar solvents.

11. The dispersion according to claim 9,
wherein
the carrier fluid includes water and/or a solvent miscible with water.

12. The dispersion according to claim 9,
wherein
pharmacologically acceptable additives are included.

13. A biochemically active compound of general formula $$S\text{-}L\text{-}Z \qquad (II),$$

the linkage sites between S and L and L and Z having covalently bound functional groups,
wherein
S represents a biocompatible substrate fixed to M represents magnetic core particle;
L represents a biocompatible linker group, and
Z represents a group comprised of nucleic acids, peptides and/or proteins or derivatives thereof, which group has at least one structure that binds to an intracellular biomacromolecule.

14. The biochemically active compound according to claim 13,
wherein
the biocompatible substrate S is a compound selected from the group consisting of poly- or oligosaccharides or derivatives thereof, such as dextran, carboxymethyldextran, starch, dialdehyde starch, chitin, alginate, cellulose, carboxymethylcellulose, proteins or derivatives thereof, such as albumins, peptides, synthetic polymers, polyethyleneglycols, polyvinylpyrrolidone, polyethyleneimine, polymethacrylates, bifunctional carboxylic acids and derivatives thereof, mercaptosuccinic acid and hydroxycarboxylic acids.

15. The biochemically active compound according to claim 13,
wherein
the linker group L is formed by reaction of a compound selected from the group consisting of dicarboxylic acids, diamines, amino acids, peptides, proteins, lipids, lipoproteins, glycoproteins, lectins, oligosaccharides, polysaccharides, oligonucleotides and alkylated derivatives thereof, and nucleic acids (DNA, RNA, PNA) and alkylated derivatives thereof, present either in single-stranded or double-stranded form, which compound includes at least two identical or different functional groups.

16. The biochemically active compound according to claim 13,
wherein
the functional groups are selected from the group consisting of —CHO, —COOH, —NH$_2$, —SH, —NCS, —NCO, —OH, —COOR,
wherein
R represents an alkyl, acyl or aryl residue and

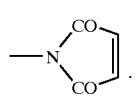

17. A method of producing magnetic nanoparticles according to claim 1, comprising the following process steps:
a. producing the magnetic core particles;
b. reacting the magnetic core particles with compound S-L-Z (II) to form compound M-S-L-Z (I).

18. A method of producing the compound of general formula (I) according to claim 1, comprising the following process steps:
a. producing the magnetic core particles;
b. reacting the magnetic core particles with the biocompatible substrate S; and
c. reacting the compound M-S having formed with a compound L-Z;
wherein
in order to produce L-Z, a compound such as poly- and dicarboxylic acids, polyhydroxycarboxylic acids, diamines, amino acids, peptides, proteins, lipids, lipoproteins, glycoproteins, lectins, oligosaccharides, polysaccharides, oligonucleotides and alkylated derivatives thereof, and nucleic acids (DNA, RNA, PNA) and alkylated derivatives thereof, present either in single-stranded or double-stranded form, which compound includes at least two identical or different functional groups, is reacted with nucleic acids, peptides and/or proteins or derivatives thereof having at least one functional group and including at least one structure that binds to an intracellular biomacromolecule.

19. A method of producing the compound of general formula (I) according to claim 1, comprising the following process steps:
a. producing the magnetic core particles;
b. reacting the magnetic core particles with the biocompatible substrate S;
c. reacting the compound M-S having formed with compounds such as poly- and dicarboxylic acids, polyhydroxycarboxylic acids, diamines, amino acids, peptides, proteins, lipids, lipoproteins, glycoproteins, lectins, oligosaccharides, polysaccharides, oligonucleotides and alkylated derivatives thereof, and nucleic acids (DNA, RNA, PNA) and alkylated derivatives thereof, present either in single-stranded or double-stranded form, which compounds include at least two identical or different functional groups; and
d. reacting the compound M-S-L having formed with nucleic acids, peptides and/or proteins or derivatives thereof having at least one functional group and including at least one structure that binds to an intracellular biomacromolecule.

20. The method according to claim 17,
wherein
the compounds S, L and Z are linked via functional groups selected from the group consisting of —CHO, —COOH, —NH$_2$, —SH, —NCS, —NCO, —OH, —COOR,
wherein
R represents an alkyl, acyl or aryl residue and

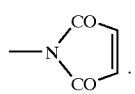

21. A method of producing the biochemically active compound according to claim 13, comprising the following process steps:
a. providing the compound L-Z,
b. reacting L-Z with the biocompatible substrate S, wherein L-Z is prepared by contacting L with Z under conditions conducive for at least one covalent bond to form between L and Z, wherein L is a compound selected from the group consisting of poly- and dicarboxylic acids, polyhydroxycarboxylic acids, diamines, amino acids, peptides, proteins, lipids, lipoproteins, glycoproteins, lectins, oligosaccharides, polysaccharides, oligonucleotides and alkylated derivatives thereof, and nucleic acids (DNA, RNA, PNA) and alkylated derivatives thereof, present either in single-stranded or double-stranded form, which compound includes at least two identical or different functional groups, and wherein Z is selected from the group consisting of nucleic acids, peptides and/or proteins or derivatives thereof having at least one functional group and including at least one structure that binds to an intracellular biomacromolecule.

22. The method according to claim 21, wherein the compounds S, L and Z are linked via functional groups selected from the group consisting of —CHO, —COOH, —NH$_2$, —SH, —NCS, —NCO, —OH, —COOR, wherein R represents an alkyl, acyl or aryl residue and

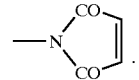

* * * * *